United States Patent [19]

Callewaert et al.

[11] Patent Number: 4,557,863
[45] Date of Patent: Dec. 10, 1985

[54] DEVICE FOR COLLECTION OF PROTEINS IN A URINAL AND METHOD OF USE

[76] Inventors: Denis M. Callewaert, 1600 Hosner Rd., Oxford, Mich. 48051; Earl J. Braxton, 46731 Shelby Rd., Utica, Mich. 48087

[21] Appl. No.: 600,081

[22] Filed: Apr. 13, 1984

[51] Int. Cl.$^4$ .................. C07G 7/00; C07G 7/026
[52] U.S. Cl. .................. 260/112 R; 422/216; 422/217; 422/253; 435/12; 435/215; 435/268; 435/288; 435/311; 435/316; 435/317; 435/296; 435/815
[58] Field of Search .................. 260/112 R; 435/288, 435/317, 215, 311, 268, 316, 12, 296, 815; 422/216, 217, 253

[56] References Cited

U.S. PATENT DOCUMENTS

| | | | |
|---|---|---|---|
| 3,711,377 | 1/1973 | Sloane | 435/215 |
| 3,755,083 | 8/1973 | Novak | 435/215 |
| 4,306,029 | 12/1981 | Carpenter | 435/268 |

*Primary Examiner*—Howard E. Schain
*Attorney, Agent, or Firm*—Krass & Young

[57] ABSTRACT

The invention relates to a device useful when installed in a urinal for collection of urinary proteins. The adsorbent means includes a conduit for gravity feed passage of urine streams. The conduit has permeable layers in series containing a slow releasing antimicrobial agent and an adsorbent for urinary proteins such that for collection puroposes wanted proteins are adsorbed without odor or loss due to bacterial degradation.

21 Claims, 3 Drawing Figures

DEVICE FOR COLLECTION OF PROTEINS IN A URINAL AND METHOD OF USE

DESCRIPTION

1. Technical Field

The invention relates to apparatus means useful when installed in a urinal for collection of urinary proteins. More particularly, the invention relates to a device and method of use comprising conduit means for gravity feed passage of urine streams therethrough and permeable layers in the conduit containing an antimicrobial agent and an adsorbent for collection of urinary proteins as an adsorbate such that the anti-microbial provides for effective inhibition of both microbial growth and consequent degradation of wanted proteins in the collected adsorbate during the period of collection.

2. Background Art

Mammalian urine contains small percentages of a variety of proteins and especially enzymes which have commercial value, usually as pharmaceuticals. For example, the enzyme urokinase, which is a plasminogen activator and is present in trace percentages in human urine, is widely used as a fibrinolytic agent in humans and in connection with treatment for cancer because of its ability to cause dissolution of the fibrin growths which sometimes sheath tumors. Most of the commercial supply of urokinase is now derived from urine by the collection of urine from paid donors who regularly visit central collection stations. Within a few hours of being collected the urine is transported to a central processing station where it is intermixed with adsorbents that attract the large protein molecules of interest. The collected proteins are then eluted off the adsorbents and the extract is processed and purified to derive the urokinase or other commercially useful proteins. U.S. Pat. No. 3,755,083 discloses a process of this type. It is also known to collect urokinase on an adsorbent placed in a urinal as illustrated by U.S. Pat. No. 3,711,377. Exemplary known adsorbents for urokinase include bentonite (U.S. Pat. No. 3,555,361), and Florosil, charcoal, and aluminum oxide. Other urinary substances of importance are peptide hormones such as human growth hormone (The Merck Index, monograph 7290, 9th Ed.), glycoproteins such as erythropoetin (Merck 3610), and the like.

Urinary proteins rapidly degenerate at normal collection temperatures so that it is necessary to process the urine either during collection or as soon as possible thereafter. The resulting collection and processing costs and the low percentage of wanted proteins such as urokinase contained in urine result in a very high unit cost, severely limiting pharmaceutical use of the materials.

SUMMARY AND DETAILED DESCRIPTION OF THE INVENTION

The present invention is directed to a novel device for the collection of urinary proteins comprising a columnar conduit or cartridge containing in series an anitbacterial component and adsorbent for proteins. The device is useful when installed in a urinal for collection of urinary proteins, especially human urinary proteins, as an adsorbate, for later isolation and purification of its content of valuable urinary proteins having application, e.g., as pharmaceutically active agents in human or veterinary medicine. The adsorbent means more particularly comprises a columnar conduit adapted for gravity feed passage of urine streams therethrough, and first and second urine-stream permeable layers in the conduit, the first and second layers comprising respectively a leachable antimicrobial agent and a suitable adsorbent for urinary proteins.

The columnar conduit, for purposes of the invention, can be any suitable open-ended container such as a pipe or plastic tube, sieve, or container removably placed in a urinal, allowing gravity flow therethrough of urine streams but so placed that water for flushing, if any, is by-passed, that is to say, the flow through the conduit does not include water flow. The first permeable layer in the conduit contains a leachable water soluble hydrophilic component comprising (1) a water soluble antimicrobial that is leached ratably by exposure to intermittent urine streams and (2) a water-insoluble hydrophobic component that sublimes ratably to the air, the respective rates of leaching and subliming during the service life being chosen such that the leaching of antimicrobial from the first layer into the second layer is sufficient to provide an inhibitor concentration effectively inhibiting microbial degradation of wanted proteins contained in the adsorbate of the second layer. The hydrophilic component of the first layer comprises a water-soluble antimicrobial agent (sometimes referred to herein as an antibacterial). The antimicrobial agent is an antimicrobial substance or mixture of antimicrobial substances that is compatible with the adsorbent and the urinary proteins and that serves to inhibit the degradation of urinary proteins in the adsorbate of the second layer as by elimination of bacterial growth and hence bacterial degradation of urinary proteins such as urokinase and the like. A preferred antimicrobial agent, for purposes of the invention, is one that inhibits microbial degradation of urokinase. For this purpose, one may use any suitable water-soluble antibacterial substance that is effective in preventing or inhibiting degradation of the desired urinary proteins. Preferred anti-microbials are water-soluble salts of pyrithione, preferably sodium pyrithione (also known as sodium omadine or 2-pyridinethiol 1-oxide, sodium salt), or a watersoluble azide salt, preferably sodium azide. The hydrophobic component of the first layer is any suitable water-insoluble aromatic hydrocarbon or halogenated hydrocarbon or mixture thereof that sublimes continuously in air at ambient room temperatures ranging, for example, from about 50 to about 100 degrees F. A preferred hydrophobic component, for purposes of the invention, is p-dichlorobenzene or naphthalene. The first layer can take any suitably permeable form which may be conventional. The first layer, for example, can comprise shaped pellets of a homogeneous mixture of the hydrophobic and hydrophilic components or it can be laminated or formed with the hydrophilic component as small particulates spaced or distributed uniformly throughout a permeable matrix of the hydrophobic component. The invention contemplates that, for collection of the urine proteins, the adsorbent means is installed either in a conventional urinal with means for by-passing flushing water or in a urinal of the type where it is exposed to air and intermittent urine streams but not exposed to flushing water, as for example a portable toilet having an unflushed urinal with gravity feed through a flow line such as that described in the patent to Braxton, U.S. Pat. No. 4,285,077.

The hydrophilic and hydrophobic components may contain a suitable deodorizing or sanitizing substance which may be conventional, or other excipient or a diluent. As contemplated, when the collection device of the invention is exposed to the air (as when installed on a mesh screen in the flow line of a toilet such as described above), the hydrophobic component undergoes continuous sublimation while so exposed at a rate depending on the air temperature. Thus, the content of subliming hydrocarbon is gradually diminished over the period of the operative service life of the collection device. When the device is exposed to the intermittent urine streams, the latter serve to leach any of the hydrophilic component that is exposed by the mentioned continuing sublimation of the hydrophobic component. In other words, the release of the water-soluble component is a discontinuous slow release coinciding with exposure to the intermittent urine streams occurring during the predetermined service life of the device. Such release of the antimicrobial, for purposes of the invention, is important because as the adsorption in the second layer increases, the protein in the adsorbate requires to a corresponding extent of increasing inhibition of bacterial action that would otherwise result in bacterial degradation of the protein. The relative content and quantities of the hydrophilic and hydrophobic components in the first layer of the adsorbent means are subject to considerable variation depending on the operating conditions. For example, where the hydrophilic component is about 5 parts by weight of an antibacterial such as sodium azide or sodium omadine and the hydrophobic component is about 95 parts by weight of a sublimeable hydrocarbon such as para-dichlorobenzene or naphthalene, sublimation and leaching from such a first layer weighing about 20 g. are satisfactory at room temperature over a service life of about 96 hours for an average total flow-through volume of about 80 liters. An unexpected feature is that release of the antibacterial is sufficient to inhibit bacterial growth and odor in the second layer of the conduit.

The second urine-stream permeable layer in the conduit, as indicated, contains adsorbent material for urinary proteins which, for purposes of the invention, may be a conventional adsorbent. The adsorbent material, for this purpose, can be any suitable solid phase material that serves to effectively adsorb the wanted urinary proteins from the fluid streams for a predetermined period or service life. The adsorbent suitably may be in the form of a bed of macroporous solids, pellets or equivalent form of suitable depth supported in the column or conduit by suitable means such as a screen, woven cloth or a base member having spaced openings or perforations allowing for support of the bed as well as gravity flow of fluid through the layers. The first and second layers preferably are spaced apart for purposes of maximizing exposure of the first layer to air sublimation. Preferred materials for adsorption are macroporous ion-exchange resins such as IRC-50 resin, of suitable mesh size such as 16-50 mesh. IRC-50 resin, for example, adjusted by pretreatment to the acid side advantageously binds about 4% of the total proteins in whole human urine but 60% of the urokinase. Bound proteins are then eluted from the resin by increasing the ionic strength or the pH. Advantageously, less than about 250 g. of IRC-50 resin is sufficient for extraction of urokinase from up to 80 liters of whole urine. Also, the resulting resin with adsorbate can be frozen for a period and then thawed at a later time as desired without appreciable loss of urokinase activity.

The invention in another aspect relates a method of collecting urine proteins. The method comprises the steps of installing in a urinal the collection device as described above comprising a conduit and first and second urine-stream permeable layers in the conduit and subjecting the permeable layers of the conduit to contact with air and intermittent flow of gravity-fed urine streams under conditions affording leaching of the antimicrobial from the first layer into each of the urine streams and adsorption onto the second layer of urinary proteins from each of the resulting leachate streams. Thus, by this method the resulting adsorbed urinary proteins are advantageously isolated as a recoverable solid phase adsorbate in the second layer, substantially free of odor and bacterial degradation of the adsorbed protein.

BRIEF DESCRIPTION OF THE DRAWING

The invention will be more fully understood by reference to the following detailed description and accompanying drawings in which.

DESCRIPTION OF PREFERRED EMBODIMENTS AND BEST MODE FOR PRACTICING THE INVENTION

Figure 1:
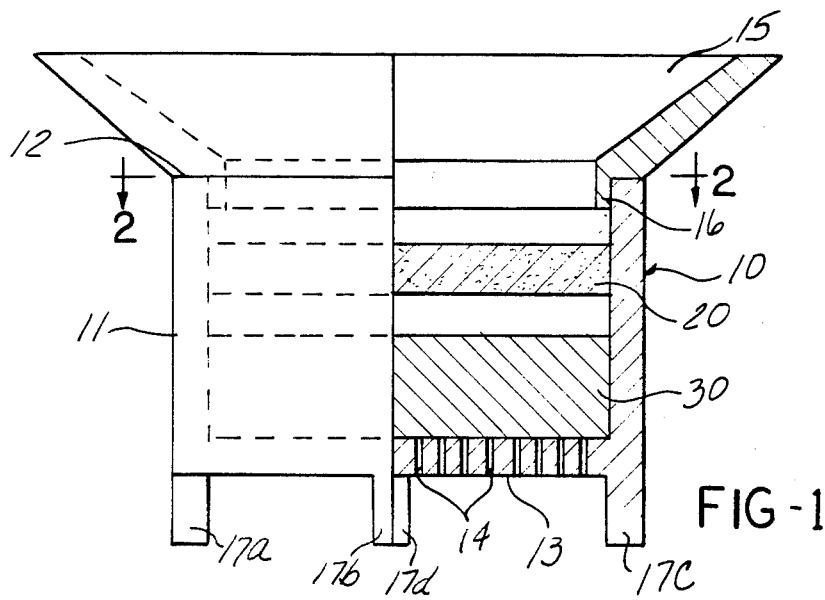
FIG. 1 is a view in elevation, partly in section taken on line 1—1 of FIG. 2, of a preferred embodiment of a collection device with a removable funnel attachment, according to the invention.
Figure 2:
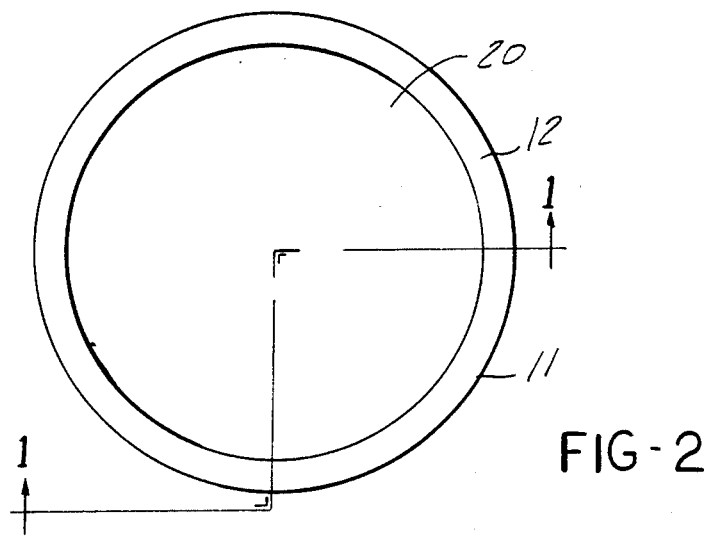
FIG. 2 is a top view of the collection device of FIG. 1 with the funnel attachment removed.
Figure 3:
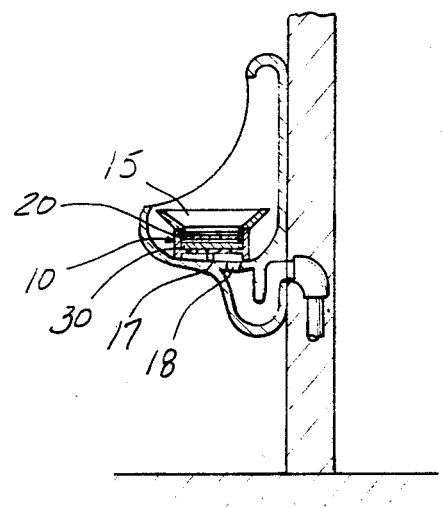
FIG. 3 is a side view, in section, of a urinal in which a collection device is installed.

Referring to the drawings, the adsorbent conduit 10 of FIG. 1 as shown has a cup-like cylindrical body 11 of suitable dimension (e.g., ca. 5 inch axial passage by ca. 6 inch diametral) that is open at the top edge 12 and partly open at the base 13 through spaced perforations 14 distributed uniformly over the base allowing for passage by gravity of urine streams downward into the open top through the conduit and outflow through the perforations 14 to a drain and waste reception means (not shown). The body 11 is provided at the top edge 12 with a funnel 15 having a shoulder 16 nesting removably within the top edge to facilitate collection and passage of urine streams into and through the adsorbent conduit. In a preferred embodiment shown in FIG. 3, for purposes of maximizing the collection volume, the top opening of the funnel 15 can be shaped to substantially cover the horizontal cross-section of the urinal but without touching the walls of the urinal, especially the back walls of the urinal, so that flushing water flows freely down the walls to the drain, substantially without touching the device, especially the funnel. In other words, flushing water (which is usually tap water) purposely, is not collected in the funnel. The base 13 is provided with feet 17a, 17b, 17c and 17d spaced apart so that the conduit can be placed in a urinal for collection purposes in a location over the urinal drain 18, FIG. 3, in which location the feet 17 are made to straddle the drain so that the water flushing the urinal can pass downwardly around and under the conduit body 11 to the drain without passing into or through the conduit. As seen in FIGS. 1 and 2 the open top end of the conduit 10 presents a uniform flat surface of a first layer 20 comprising hydrophilic and hydrophobic components that cooperate, on exposure to air and intermittent urine streams as described above, to slowly release the leachable antimicrobial. The first layer 20 can take the form of a solid cake as shown, suitably perforated to make the layer permeable or it can take the form of one or more pellets or blocks supported on a screen and spaced above the second layer. As indicated, below the first layer is a second layer 30 containing adsorbent for urinary proteins. Preferably, the first layer is spaced axially above the second layer at a sufficient distance such that the first layer is kept exposed to air when not exposed to intermittent fluid stream or, in other words, fluid flow backup from the second layer to the first layer is avoided. In operation, during exposure to air, the hydrophobic component of the first layer 20 sublimes continuously thereby gradually exposing the leachable antimicrobial of the hydrophilic component for slow release. During exposure to each intermittent urine stream, the incremental quantity of leachable antimicrobial thus exposed is leached by the stream from the first layer 20 into the second layer 30. In the second layer, urinary proteins of the urine stream are adsorbed onto the adsorbent contained in the second layer thereby removing the proteins from the passing stream. At the same time, some of the antimicrobial is entrained in the second layer so that bacterial action and consequent bacterial degradation of the protein adsorbate are inhibited. It is an important feature of the invention that the conduit device 10 serves to prevent flow of flushing water through the conduit. Thus, not only is the antimicrobial leached only by intermittent urine streams but also the adsorbent layer 30 is not exposed to large amounts of water containing undesirable ions such as calcium or zinc ions that if adsorbed would shorten the useful life of the adsorbent. After the adsorbent conduit unit has served its purposes for collection of protein, it is removed and replaced with a fresh unit, and the wanted protein in the replaced unit is removed by elution of the adsorbate for further processing as desired. In one preferred embodiment, the collection device 10 is made by loading the second layer 30 (onto a screen support) as a uniform bed of macroporous adsorbent such as ion-exchange resin IRC-50 (e.g., 350 grams) and then inserting on a support (not shown) the first layer 20 containing a homogeneous mixture of para-dichlorobenzene (95 parts by weight) and sodium amodine (5 parts by weight) in solid cake form (i.e., a solidified suspension of the sodium amodine in melted dichlorobenzine) made permeable to urine flow by perforating the cake uniformly for axial flow through the layer. The layers 20 and 30 can if desired be supported upon open mesh screens.

What is desired to claim as my exclusive property in the invention, as described, is the following:

1. A device for installation in a urinal useful for collection of urinary proteins, comprising an open ended columnar conduit for gravity feed passage of urine streams therethrough, and first and second urine stream permeable layers in the conduit, the first and second layers containing respectively (1) a leachable water soluble hydrophilic component comprising an antimicrobial agent and (2) an adsorbent for urinary proteins, the water soluble hydrophilic component including a water soluble antimicrobial that is leached ratably by exposure to intermittent urine streams and a water insoluble hydrophobic component that sublimes ratably to the air thereby gradually exposing the hydrophilic component for slow release, the respective rates of leaching and subliming during the service life being chosen such that the leaching of antimicrobial from the first layer into the second layer is sufficient to provide an inhibitor concentration effectively inhibiting microbial degradation of wanted proteins contained in the adsorbate of the second layer.

2. A device according to claim 1 where the antimicrobial agent specifically inhibits bacterial degradation of urokinase.

3. A device according to claim 1 where the antimicrobial agent comprises a water soluble salt of pyrithione.

4. A device according to claim 1 where the antimicrobial agent comprises sodium pyrithione.

5. A device according to claim 1 where the antimicrobial agent comprises sodium azide.

6. A device according to claim 1 where the first layer contains a hydrophobic component comprising p-dichlorobenzene.

7. A device according to claim 1 where the first layer contains a hydrophobic component comprising naphthalene.

8. A device according to claim 1 where the first layer comprises a homogeneous mixture of sodium pyrithione and p-dichlorobenzene.

9. A device according to claim 1 where the first layer comprises a mixture containing by weight about 5 to about 10% of antimicrobial agent and about 90 to about 95% of a hydrophobic component that sublimes on exposure to air.

10. A device according to claim 9 where the antimicrobial is sodium pyrithione and the hydrophobic component is p-dichlorobenzene.

11. A device according to claim 1 where the adsorbent is an adsorbent of urokinase.

12. A device according to claim 1 where the adsorbent is an ion-exchange resin.

13. A method of collecting urine proteins comprising the steps of installing in a urinal the device according to claim 1 comprising a conduit and first and second urine-stream permeable layers in the conduit and subjecting the permeable layers of the conduit to contact with air and intermittent flow of gravity-fed urine streams under conditions affording leaching of the antimicrobial agent from the first layers into each of the urine streams and adsorption onto the second layer of urinary proteins from each of the resulting leachate streams thereby isolating the resulting adsorbed urinary proteins as a recoverable solid phase adsorbate in the second layer in which layer the antimicrobial leachate inhibits degradation of the adsorbed protein.

14. A method according to claim 13 where the antimicrobial agent specifically inhibits the degradation of urokinase.

15. The method according to claim 13 where the hydrophilic component comprises a water soluble salt of pyrithione.

16. The method according to claim 13 where the hydrophilic component comprises sodium pyrithione.

17. The method according to claim 13 where the hydrophilic component comprises sodium azide.

18. The method according to claim 13 where the first layer contains a hydrophobic component comprising p-dichlorobenzene.

19. The method according to claim 13 where the first layer comprises a homogeneous mixture of sodium pyrithione and p-dichlorobenzene.

20. The method according to claim 13 where the adsorbent is an adsorbent of urokinase.

21. The method according to claim 13 where the adsorbent is an ion-exchange resin.

* * * * *

UNITED STATES PATENT AND TRADEMARK OFFICE
CERTIFICATE OF CORRECTION

PATENT NO. : 4,557,863
DATED : December 10, 1985
INVENTOR(S) : Denis M. Callewaert, Earl J. Braxton It is certified that error appears in the above—identified patent and that said Letters Patent are hereby corrected as shown below:

In the Abstract, line 7 "puropses", should be --purposes--.

Column 3, line 21 "of" should be --an--.

Signed and Sealed this

Twenty-fourth Day of June 1986

[SEAL]

Attest:

DONALD J. QUIGG

Attesting Officer

Commissioner of Patents and Trademarks